United States Patent [19]

Yahagi et al.

[11] Patent Number: 4,727,162

[45] Date of Patent: * Feb. 23, 1988

[54] MOLECULAR COMPOUND OF FLUORAN COMPOUND AND KETONE

[75] Inventors: Masakichi Yahagi, Tokyo; Tetsuo Igaki, Kawagoe, both of Japan

[73] Assignee: Shin Nisso Kako Co., Ltd., Tokyo, Japan

[*] Notice: The portion of the term of this patent subsequent to Sep. 22, 2004 has been disclaimed.

[21] Appl. No.: 934,704

[22] Filed: Nov. 25, 1986

Related U.S. Application Data

[63] Continuation-in-part of Ser. No. 789,950, Oct. 21, 1985, Pat. No. 4,695,640.

[30] Foreign Application Priority Data

Oct. 24, 1984 [JP] Japan ................. 59-223460

[51] Int. Cl.$^4$ .......................................... C07D 311/96
[52] U.S. Cl. ................................................ 549/226
[58] Field of Search ........................................ 549/226

[56] References Cited

U.S. PATENT DOCUMENTS 4,444,591  4/1984  Kawai et al. ............... 549/226 X
4,642,357  2/1987  Yahagi et al. ............... 549/226

Primary Examiner—Richard L. Raymond
Attorney, Agent, or Firm—George B. Oujevolk

[57] ABSTRACT

A molecular compound of a fluoran compound and a ketone useful as a color former for heat or pressure-sensitive color-developable recording material.

3 Claims, 2 Drawing Figures

1

MOLECULAR COMPOUND OF FLUORAN COMPOUND AND KETONE

This application is a continuation-in-part of application Ser. No. 789,950 filed Oct. 21, 1985, now U.S. Pat. No. 4,695,640.

FIELD OF THE INVENTION

This invention relates to a novel compound prepared from fluoran compound and ketone and more particularly to a color developable substance with high color developable ability which can be used for the color developable recording material utilizing the heat sensitive or pressure sensitive color development.

DESCRIPTION OF THE PRIOR ART

The high speed of facsimile communication necessitates the improvement of the color developing rate (color developability) of a color developing dye because most of such high speed communication is using the heat sensitive recording paper having on the surface thereof the layer containing a color developing dye (hereinafter referred to as "color developing dye" or "color former"), which is ordinarily colorless or light colored and developes color by the action of an acidic substance and a color developer (the acidic substance) to develop the dye heat sensitively. There is highly desired the improvement of the color developing properties of the dye as well as the improvement of color developer and sensitizer.

As a color developing dye, particularly a black color developing dye, for the heat sensitive recording paper, the fluoran compounds are important. There is desired also the highly improvement of the color developing rate of these fluoran compounds. On the other side, for the pressure sensitive copying paper, the high solubility in an organic solvent used for production of the paper is desired to a color developing dye.

Japanese patent publication (before examination) Tokkaisho No. 59-19463 (1984) and UK Patent application GB No. 2141727 A disclose 3-N-isobutylethylamino-6-methyl-7-phenylaminofluoran having a following formula (I) (hereinafter referred to as "the Fluoran").

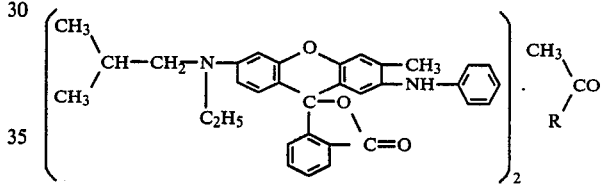

The Fluoran is a black color developing dye, and is superior in color developing late and in solubility in an organic solvent. This invention intends to improve these performances of the Fluoran furthermore.

SUMMARY OF THE INVENTION

The inventors have found that the Fluoran can form the molecular compound with ketone and found that the heat sensitive recording paper containing these novel compounds developes the color easily as compared with one containing the Fluoran not combined with ketone and that the novel compound has greater solubility compared with the Fluoran in an organic solvent used for pressure sensitivity copying paper.

Accordingly, it is an object of this invention to provide a novel compound with high sensitivity in use for color developing materials such as the heat sensitive recording paper and with high solubility in an organic solvent used for the pressure sensitive copying paper.

It is another object of the invention to provide a heat sensitive color developing recording material, which has high sensitivity.

It is another object of the invention to provide a pressure sensitive copying paper, which has high sensitivity.

The foregoing and other objects of the present invention can be attained by the following:

DETAILED DESCRIPTION OF PREFERRED EMBODIMENTS

This invention is a novel compound of the formula

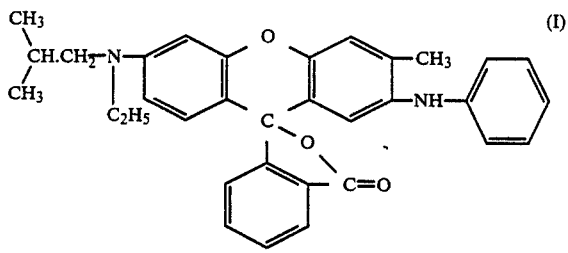

wherein R methyl or ethyl ($CH_3-$ or $C_2H_5-$).

The novel compound can be produced by just contacting of the Fluoran with the ketone of acetone or methylethyl ketone. For this production more than theoretical amount of ketone to the Fluoran can be employed. When enough amount of ketone to contact with a hole crystal of the Fluoran is employed, the novel compound can be formed very rapidly. But when theoretical amount or nearly theoretical amount of ketone is used, it takes more time for the novel compound to be produced because diffusion of ketone to a hole of the Fluoran is too time-consuming. The contact can be carried out at ordinary or a lower temperature and the reaction rate can be expedited by heating.

In a part where a crystal of the Fluoran contacts with the ketone the novel compound can be formed in a moment at ordinary or higher temperature, however total time for a hole amount of Fluoran to change to the novel compound depends on size of the Fluoran crystal, an amount of ketone employed and the temperature.

Ordinary, the novel compound can be obtained by dissolving the Fluoran in the ketone and by precipitating the novel compound in the ketone by means of distillation or cooling. Namely, the novel compound is obtained in Example 1 of this invention by dissolving the Fluoran in the ketone under heating and then by cooling to precipitate the crystal of the novel compound. Further, the novel compound can be obtained by the treatment, as shown in the Example 2, that the Fluoran is mixed with the ketone at room temperature to obtain slurry and the slurry is allowed to stand for a long time without heating. Furthermore, a nearly same amount to theoretical amount of the ketone can be used as shown in the Example 3, in which about 2 times of theoretical amount of ketone is employed (molecule ratio: the Fluoran/acetone=1:1.03). In the Example 3, it takes long time to obtain the novel compound because diffusion of ketone to a hole of the Fluoran is too time-consuming.

The formation of molecular compound of fluoran compound and ketone does not occur to all of the fluoran compounds, and there is found high selectivity depending on the structure of the fluoran compounds.

For example, the fluoran compounds of the formula

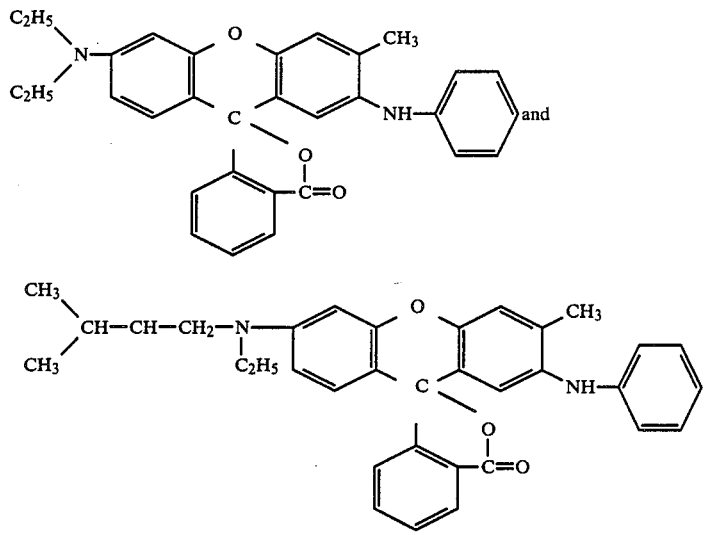

can not form any molecular compound with acetone nor methyl ethyl ketone.

Table 1 shows melting points of the novel compounds.

Figure 1:
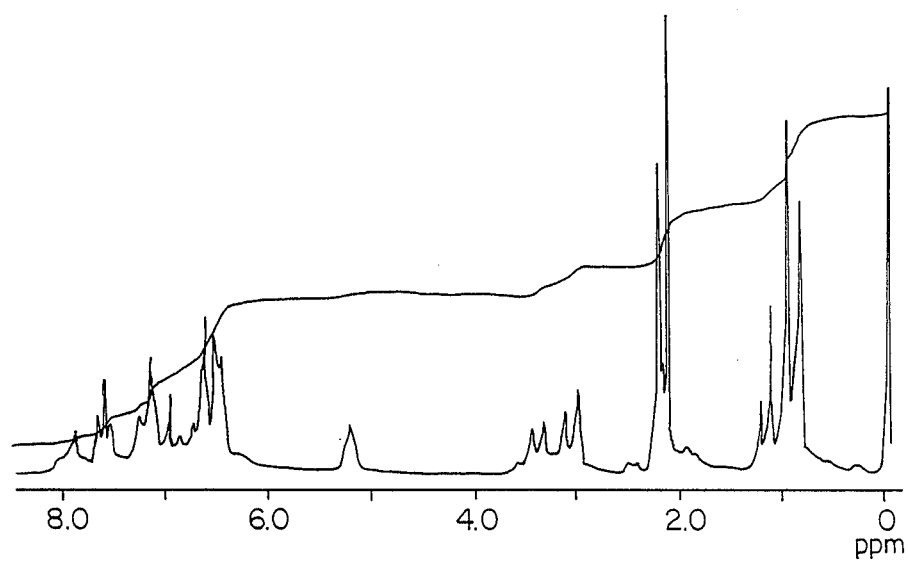
FIG. 1 shows a nuclear magnetic resonance (NMR) spectrum of the novel compound A prepared from the Fluoran and acetone.
Figure 2:
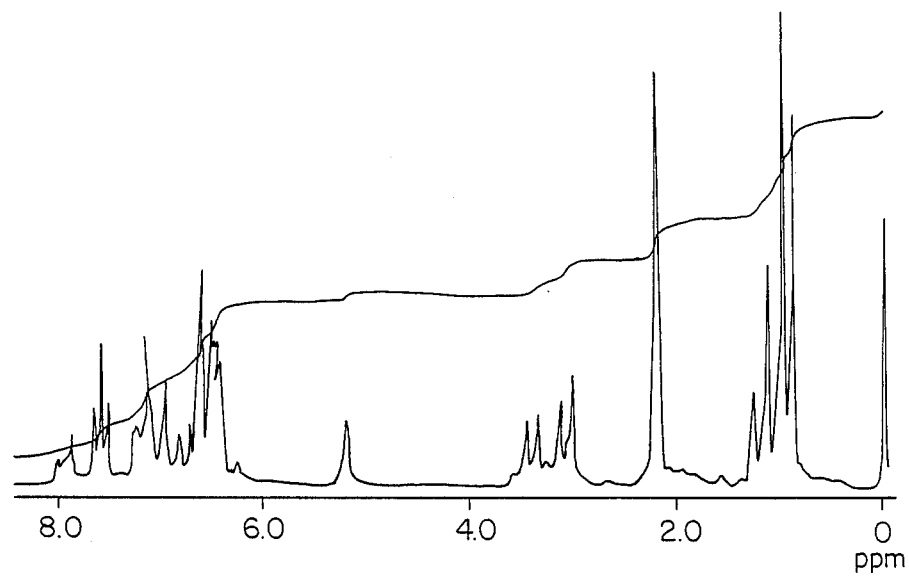
FIG. 2 shows a nuclear magnetic resonance (NMR) spectrum of the novel compound B prepared from the Fluoran and methylethyl ketone.

FIG. 1 shows an NMR spectrum of the novel compound A and FIG. 2 shows an NMR spectrum of the Fluoran itself. In FIG. 1, a signal of hydrogen in methyl group of acetone appears at (delta) 2.18 ppm, and its integrated intensity is equal to the integrated intensity of the signal of hydrogen of methyl radical at 6-position of the fluoran compound found at (delta) 2.22 ppm. Therefore, it is understood that one molecule of acetone is added to 2 molecules of the Fluoran in the novel compound A.

In the NMR spectrum, $CD_3Cl$ is used as a solvent and TMS is used as a standard substance.

In the Table 2, the results of elemental analysis of the novel compounds A and B are shown and from the results it is appear that the novel compounds A and B consist of 2 molecules of the Fluoran and 1 molecule of the ketone.

Further in the infrared spectrum, the novel compound A shows a clear absorption at about $1,710 \text{ cm}^{-1}$ and the novel compound B shows at $1,700 \text{ cm}^{-1}$, which arise from a radical of $=c=o$ of ketone, on the otherhand a absorption of $=c=o$ of lactone ring of fluoran appears at $1740 \text{ cm}^{-1}$.

These novel compounds dissociate into the original Fluoran and ketone by heating to melt and further, when the novel compound is dissolved in n-butyl alcohol and distilled to remove n-butyl alcohol, crystals of original Fluoran can be precipitated as a distillation residue. Furthermore the novel compound is insoluble in n-hexane and when crystal of the novel compound is mixed with n-hexane and heated, it changes to crystal of the original Fluoran.

From these facts, it is strongly suggested that the ketone is combining with the Fluoran as a crystal solvent.

Table 3 shows solubilities (g/100 g of solvent) of the novel compounds A and B and the Fluoran at 50° C. in an organic solvent (di-isopropylnaphthalene, which is widely used in pressure sensitive copying paper).

As shown in the Table 3, the novel compounds A and B show higher solubilities in organic solvents than the Fluoran and this property is fitting to the production of a pressure sensitive copying paper.

Table 4 shows that the heat sensitive recording paper made from the novel compound of this invention has extremely high color developability by heat as compared to the one made using the Fluoran itself. In Table 4, the higher numerals indicate the higher density of the resulting color. The color developers used in these experiments are 2,2-bis(p-hydrophenyl)propane (bisphenol A) and benzyl p-hydroxylbenzoate (P-HBAB).

The method of production of heat sensitive recording paper using the novel compound of this invention is similar to that using the known color developing dye, for example, as disclosed in Japanese Patent Publications (after examination) Nos. Tokkosho 39-27579 (1964), Tokkosho 43-4160 (1968) and Tokkosho 45-14039 (1970), and Japanese Patent Publication (before examination) No. Tokkaisho 59-7087 (1984). In the other words, the heat sensitive recording paper having excellent color developability can be produced by dispersing finely divided particles of the novel compound of this invention and finely divided particles of a color developer into an aqueous solution of a water soluble binding agent to form the suspension, applying the suspension to the surface of paper to form a heat sensitive layer, and drying. Further if a sensitizer is added to the suspension, the heat sensitive recording paper having extremely high sensitivity can be produced. The suspension can contain further a filler, a dispersing agent, a color stabilizing agent, an anti-oxidant, a desensitizer, an anti-tack agent, an anti-foaming agent, a light sensitizer, a fluorescent brightening agent and etc.

Other than the aforementioned bisphenol A and P-HBAB, there may be listed as a color developer, bisphenol compounds such as 4,4'-secondary-butylidene bisphenol, 4,4'-cyclohexylidene bisphenol, 2,2'-dihydroxyldiphenyl, pentamethylene-bis(4-hydroxylbenzoate);

sulphur-containing bisphenol compounds such as 1,7-di(4-hydroxyphenylthio)-3,5-dioxaheptane;

4-hydroxybenzoicacid esters such as ethyl 4-hydroxybenzoate, propyl-4-hydroxybenzoate, isopropyl-4-hydroxybenzoate, butyl-4-hydroxybenzoate, isobutyl-4-hydroxybenzoate, chlorobenzyl-4-hydroxybenzoate, methylbenzyl-4-hydroxybenzoate, diphenylmethyl-4-hydroxybenzoate;

hydroxy sulfones such as 4-hydroxy-4'-methyldiphenylsulfone, 4-hydroxy-4'-isopropoxydiphenylsulfone, 4-hydroxy-4'-butoxydiphenylsulfone;

4-hydroxyphthalic acid diesters such as dimethyl-4-hydroxyphthalate, dicyclohexyl-4-hydroxyphthalate, diphenyl-4-hydroxyphthalate;

esters of hydroxynaphtoeic acid such as 2-hydroxy-6-carboxynaphthalene;

and futher hydroxyacetophenone, p-phenylphenol, benzyl-4-hydroxyphenylacetate, p-benzyphenol, hydroquinone-monobenzyl ether.

There can be mentioned, as a water soluble binding agent, polyviny alcohol, hydroxyethyl cellulose, carboxymethyl cellulose, salt of styrenemaleic anhydride copolymer, styrene-butadiene emulsion, vinylacetate-maleic anhydride emulsion, salt of polyacrylic acid, polyacryl amide, starchs, casein, gum arabic, and the like. But, it can not be restricted to these materials.

There can be mentioned, as a sensitizer, higher fatty acid amide, benz amide, stearic acid anilide, acetoacetic acid anilide, thioaceto anilide, dimethyl phthalate, dibenzyl terephthalate, dibenzyl isophthalate, bis(tert-butylphenols), diethers of bisphenol S such as 4,4'-dimethoxy diphenylsulfone, 4-iso-propoxyl-4'-n-butoxydiphenylsulfone, 4,4'-dibutoxy diphenylsulfone, 4,4'di-n-(or iso-)pentyloxydiphenylsulfone; diphenyl amine, carbazole, 2,3-di-m-torylbutane, 4,4'-dimethyl biphenyl, di-$\beta$-naphthyl phenylenediamine.

There can be mentioned, as a filler, clay, talc kaoline, satine white, titanium oxide, calcium carbonate, magnesium carbonate, barium sulfate, magnesium silicate, aluminium silicate, and the like.

There can be mentioned, as a dispersing agent, sulfosuccinic acid ester such as sodium dioctylsuccinate, sodium dodecylbenzenesulfonate, sodium salt of laurylalcoholsulfate ester, salt of fatty acid and the like.

There can be mentioned, as a color stabilizing agent, metal salt, preferrably zinc salt of salicylic acid derivatives and oxynaphtoeic acid derivatives, and water insoluble zinc compounds.

There can be mentioned, as an antioxidant, 2,2'-methylene-bis(4-methyl-6-tert-butylphenol), 2,2'-methylenebis(4-ethyl-6-tert-butylphenol), 4,4'-propyl-methylenebis(3-methyl-6-tert-butylphenol), 4,4'-thiobis(2-tert-butyl-5-methylphenol), and the like.

There can be mentioned, as a desensitizer, alliphatic higher alcohol, polyethylene glycol, guanidine derivatives and the like.

There can be mentioned, as an anti-tack agent, stearic acid, zinc stearate, calcium stearate, carnauba wax, paraffin wax, ester wax and the like.

It should be noted that the novel compound of this invention can be used in the pressure sensitive copying paper. The method of application of the novel compound to the said use is similar to that of the general fluoran compounds, as disclosed in U.S. Pat. Nos. 2,548,365, 2,548,366, 2,800,457 and 2,800,458 and Japanese Patent Publications (before examination) Nos. Tokkaisho 58-11204 (1983) and Tokkaisho 58-139738 (1983) so that the significant pressure sensitive copying paper can be produced by such disclosed methods. The usable developer can be the conventional known developer, for example, inorganic acidic material such as acid clay, activated clay, attapulgite, bentonite, colloidal silica, aluminium silicate, magnesium silicate, zinc silicate, tin silicate, calcined kaoline, talc; aliphaticcarboxylic acid such as oxalic acid, maleic acid, tartaric acid, citric acid, succinic acid, stearic acid;

aromatic carboxylic acid such as benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid;

3-phenyl-5-($\alpha,\alpha$-dimethylbenzyl)salicylica acid, 3,5-di-(2-methylbenzyl)salicylic acid, 2-hydroxy-1-benzyl-3-naphthoeic acid, salt of those aromatic carboxylic acid with metal such as zinc, magnesium, aluminium, titanium;

phenol resin developer such a p-phenylphenol formaline resin and p-butylphenol-acetylene resin;

the mixture of those phenol resin developer with the said metal salt of aromatic carboxylic acid and the like.

The novel compound of this invention can be used as a color former for a recording paper in a heat sensitive transfer method, a electro conductive recording paper, electronic photography using a developing agent of toner containing acidic substance, stamp ink, and an ink ribbon for typewriter, other than for a heat sensitive recording paper and a pressure sensitive copying paper. The heat sensitive transfer system can utilize the inventive product, for example, in the method disclosed in Japanese Patent Publication (before examination) Nos. Tokkaisho 58-212985 (1983), 58-33185 (1983) and 59-42995 (1984).

Further, the novel compound of this invention can be used in the electro conductive recording paper as disclosed in Japanese Patent Publication (before examination) Nos. Tokkaisho 48-96137 (1973), Tokkaisho 48-101935 (1973) and Tokkaisho 49-11344 (1974).

The novel compound of this invention can be used in the electro photography as disclosed in Japanese Patent Publication (before examination) Nos. Tokkaisho 52-24530 (1977) and 52-56932 (1977).

It should be noted that the novel compound of this invention can be used in the mixture with the other color formers.

The following examples illustrate the practice of the invention, but should not be interpreted for the limitation of the invention.

EXAMPLE 1: PREPARATION OF NOVEL COMPOUND A 30.0 G of the Fluoran was added to 300 ml of acetone and refluxed for 20 minutes and cooled to precipitate fine white crystals. This precipitate was filtered and dried, yielding 20.3 g of the novel compound A which has a melting point at 139° C. to 141° C. The NMR spectrum (FIG. 1) thereof indicates that those crystals are the compound of two molecules of the Fluoran and one molecule of acetone.

EXAMPLE 2: PREPARATION OF NOVEL COMPOUND A 30.0 G of the Fluoran was added to 300 ml of acetone and the slurry was allowed to stand for 10 hours at room temperature under agitation. Then the slurry was filtered and evacuated at room temperature to remove acetone as far as acetone on the surface disappeared and dried at 80° C. for 6 hours. Obtained white crystal was 20.8 G and had melting point of 137°–143° C. The NMR spectrum thereof showed as same pattern as FIG. 1.

EXAMPLE 3: PREPARATION OF NOVEL COMPOUND A 1.04 G of the Fluoran was weighed out in a 30 ml weighing bottle, 0.123 g of acetone (molecula ratio: fluoran/acetone=1:1.03) were added in the bottle and then the bottle was titely pluged. All the acetone seemed to be absorbed in the crystal of the Fluoran. The mixture was allowed to stand for 5 days at room temperature. The bottle was evacuated at room temperature for 1 hour to remove remaining acetone and placed in a dryer at 80° C. for 6 hour to dry the crystals. Melting point of white crystal so obtained was 136°–143° C. and the NMR spectrum thereof showed almost same pettern as FIG. 1. From the NMR spectrum, it is indicated that the white crystals consist of two molecules of the Fluoran and one molecule of acetone.

EXAMPLE 4: PREPARATION OF NOVEL COMPOUND B 30.0 G of the Fluoran was added to 30 ml of methylethyl ketone and heated. The Fluoran was dissolved completely before boiling but the reflux was continued for 10 minutes. Cooling to precipitate crystals and then the crystals were filtered and dried and 20.7 g of white crystals of novel compound B were obtained. The melting point thereof was 128.0° C. to 129.0° C.

EXAMPLE 5: (APPLICATION EXAMPLE)

3.5 G of the novel compound A, as a color former, 41.5 g of a 15% aqueous solution of polyvinyl alcohol (commercially available from Kurare Corporation as "Kurare 105"), 15.0 g of clay (commercially available from Engelhart Corporation as "UW-90") and 40.0 g of pure water were put together with 150 g of glass beads (1 to 1.5 mm in size) in a polyethylene bottle of 250 ml and sealed. The bottle was mounted on a paint conditioner manufactured by Red Devil Company and shaken for five hours at the frequency of 630/minute. Then the glass beads were removed from the mixture yielding the aqueous suspension of the novel compound A (Suspension A).

On the other hand, 10.5 g of bisphenol A as a color developer, 41.5 g of 15% aqueous solution of polyvinyl alcohol (the above mentioned), 8.0 g of clay (the above mentioned), and 40.0 g of pure water as well as 150 g of glass beads were put in the polyethylene bottle of 250 ml and sealed. The bottle was mounted on the above mentioned paint conditioner and shaken for eight hours at the frequency of about 630/minute, and removing the glass beads to yield an aqueous suspension of bisphenol A (Suspension B).

Each 10 g of Suspensions A and B were mixed and agitated for 20 minutes to yield a coating liquid.

This coating liquid was applied to the surface of a white paper by using a wire rod No. 12, and dried for two minutes by blowing a hot air at 60° C. to produce a heat sensitive recording paper.

The applied surface of this heat sensitive recording paper was heated using a Heatgradient Tester (manufactured by Toyo Seiki Seisakusho) at 75° C., 80° C., 85° C., 90° C., 95° C., 100° C., 110° C., 120° C., and 150° C. for 5 seconds under the pressure of 1 kg/cm$^2$ to develop color, and measured the densities of resulting color on the paper surface by Macbeth reflection densitometer (filter: Ratten #106). The results were shown in Table 4.

EXAMPLE 6: (APPLICATION EXAMPLES)

Using the novel compound A as a color former and P-HBAB as a color developer, the procedures of example 5 was repeated to produce a heat sensitive recording paper. The papers were colored and the densities of the color were measured. The results were shown in Table 4.

COMPARATIVES 1 AND 2

Using the Fluoran as a color former and bisphenol A or P-HBAB as a color developer, the procedures of example 5 were repeated to produce heat sensitive recording papers, followed by color developing, measuring of the densities of developed color. The results were shown in Table 4.

EXAMPLE 7: (APPLICATION EXAMPLE)

1.0 G of novel compound A was dissolved in 20 g of di-isopropylnaphthalene (commercially available from Kureha Chemical as "KMC-113") at 90° C. (Liquid A).

2.0 G of gelatin (isoelectric point: 8.0) and 0.5 g of carboxymethyl cellulose were completely dissolved in 120 ml of water (Liquid B).

The liquids A and B were mixed at 50° C. to 60° C., and agitated in high speed to form emulsion and adjusted to pH 8.5 to 9.0. After the adjustment of pH, the high speed agitation was continued further for 20 minutes and pH of the emulsion was gradually reduced to pH 3.8 using diluted acetic acid. The emulsion was cooled to 5° C. to 10° C. with the continuing agitation and 6 g of formalin solution (35%) was added and further followed by continuing agitation for one hour at of 10° C. to 20° C.

Then, the emulsion was further adjusted to pH 9.0 by sodium hydroxide solution (5%). The resulting emulsion were further slowly agitated for several hours to yield the emulsion containing extremely finely divided capsuls encapsulated by gel membrane of carboxmethyl cellulose and gelatin, which contain the solution of novel compound A inside. This emulsion was coated on a surface of paper and dried to obtain a back coated sheet (BC sheet) of the pressure sensitive copying paper. On the other hand, phenol formalin resin was applied on the furface of a paper and dried to produce a front coated sheet (FC sheet) of the recording material. The coated surface of BC sheet was faced to the coated surface of BC sheet and one wrote down a letter on BC sheet from the upper surface of BC sheet under some writing pressure, and one found a clear letter in black color on the coated surface of FC sheet.

Further, when clay was used in place of phenol formalin resin for the above mentioned production of FC sheet, one found a clear letter in purple black color on the coating face of FC sheet.

EXAMPLE 8: (APPLICATION EXAMPLE)

4.0 G of the novel compound B was mixed with 50.0 g of alkyldiphenylmethane (commercially available from Nisseki Chemical, as "Highsol SAS 296") and 36.0 g of di-isopropylnaphthalene and heated to dissolve, and agitated at 90° C. for ten minutes and cooled (Liquid A).

On the other hand, 30.0 g of a 10% aqueous solution of sulfonic acid modified polyvinyl alcohol (commercially available from Nippon Gosei Chemical Industories, as "gosenol CK-50", the average polymerization degree of about 300, the saponification value of 97% and modification degree of 10 mol. %), 15.0 g of a 10% aqueous solution of ethylene-maleicanhydride copolymer (commercially available from Monsanto Co. as "EMA-31") and 67.5 ml of water were mixed and further 5.0 g of urea and 0.5 g of resolsinol were added and dissolved, and then adjusted to pH 3.4 by using an 20% aqueous solution of sodium hydroxide (Liquid B).

The liquid A was added to the liquid B and agitated for two minutes by using a homomixer at the rotation of 9,000 rpm, to form an emulsion, and then 14.0 g of a 35% solution of formalin was further added and agitated for 3 minutes at the rotation of 9,000 rpm and then the rotation was reduced to 8,000 rpm, heating to 60° C. to 65° C. and further the agitation was continued for 60 minutes.

Upon discontinuing the agitation by a homomixer, the mixture was cooled to 40° C. and adjusted to pH 7.5 by adding a 28% ammonia aqueous solution to produce a suspension of microcapsules.

27.0 G of this suspension, 3.5 g of wheat starch, 8.5 g of 8% wheat starch solution and 34.0 g of water were mixed by a stirrer at room temperature for 30 minutes to yield a coating liquid.

This coating liquid was applied to the surface of a white paper using a wire rod No. 12 and dried by blowing a hot air at 60° C. for 3 minutes to produce a BC sheet of the pressure sensitive copying paper.

Using this BC sheet to face FC sheet as used in Example 7, the copying procedure as in example 7 was carried out, one found a clear black letter on the surface of the FC sheet.

TABLE 1

| | Formula | Melting point (C.°) |
|---|---|---|
| this invention | the novel compound A | 139–142 |
| | the novel compound B | 128–129 |
| raw material | the Fluoran | 151–154 |

TABLE 2

| | (%) | | |
|---|---|---|---|
| | c | H | N |
| the novel compound A $(C_{33}H_{32}N_2O_3)_2 \cdot C_3H_6O$ | | | |
| theoretical value | 77.67 | 6.57 | 5.25 |
| found value | 77.72 | 6.66 | 5.22 |
| the novel compound B $(C_{33}H_{32}N_2O_3)_2 \cdot C_4H_8O$ | | | |

TABLE 2-continued

| | (%) | | |
|---|---|---|---|
| | c | H | N |
| theoretical value | 77.78 | 6.67 | 5.19 |
| found value | 77.89 | 6.68 | 5.25 |

TABLE 3

| Solubilities in di-isopropylnaphthalene (g/100 g) | |
|---|---|
| The novel compound A | 7.6 |
| The novel compound B | 7.7 |
| The Fluoran | 4.5 |

TABLE 4

| note | color former | color developer | Color developing temperature (°C.) | | | | | | | | |
|---|---|---|---|---|---|---|---|---|---|---|---|
| | | | 75 | 80 | 85 | 90 | 95 | 100 | 110 | 120 | 150 |
| example 5 | novel compound A (this invention) | bisphenol A | 0.20 | 0.23 | 0.28 | 0.40 | 0.68 | 0.87 | 1.20 | 1.30 | 1.32 |
| comparative 1 | the Fluoran | bisphenol A | 0.14 | 0.14 | 0.14 | 0.15 | 0.19 | 0.24 | 0.50 | 1.06 | 1.30 |
| example 6 | novel compound A (this invention) | P-HBAB | 0.26 | 0.51 | 0.91 | 1.13 | 1.27 | 1.32 | 1.34 | 1.36 | 1.37 |
| comparative 2 | the Flouran | P-HBAB | 0.23 | 0.37 | 0.72 | 1.06 | 1.25 | 1.32 | 1.34 | 1.36 | 1.37 |

We claim:

1. A compound of a formula:

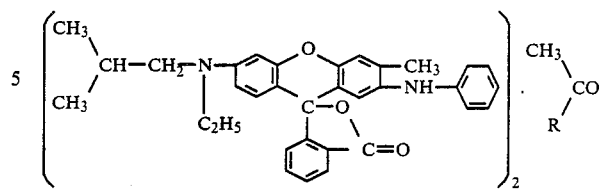

(wherein R is methyl or ethyl.).

2. A compound as claimed in claim 1, wherein R is methyl.

3. A compound as claimed in claim 1, wherein R is ethyl.

* * * * *